United States Patent [19]

Manuccia

[11] 4,070,412
[45] Jan. 24, 1978

[54] METHOD FOR PRODUCTION OF ACETYLENE BY LASER IRRADIATION

[75] Inventor: Thomas J. Manuccia, Laurel, Md.

[73] Assignee: The United States of America as represented by the Secretary of the Navy, Washington, D.C.

[21] Appl. No.: 721,649

[22] Filed: Sept. 8, 1976

[51] Int. Cl.² .............................................. C07C 11/24
[52] U.S. Cl. .............................. 260/679 R; 208/48 Q; 260/683 R; 204/DIG. 11; 204/171; 204/172
[58] Field of Search ........... 260/679 R, 679 A, 683 R; 204/DIG. 11, 171–172, 168, 80

[56] References Cited

U.S. PATENT DOCUMENTS

| 3,073,769 | 1/1963 | Doukas | 204/171 |
| 3,419,632 | 12/1968 | Sogawa et al. | 260/679 |
| 3,522,015 | 7/1970 | Maniero et al. | 260/679 |
| 3,652,447 | 3/1972 | Yant | 208/11 |
| 3,663,394 | 5/1972 | Kawahara | 204/168 |
| 3,699,210 | 10/1972 | Binning et al. | 423/447 |

Primary Examiner—Delbert E. Gantz
Assistant Examiner—G. E. Schmitkons
Attorney, Agent, or Firm—R. S. Sciascia; Philip Schneider; Melvin L. Crane

[57] ABSTRACT

Production of acetylene by pyrolytic cracking of hydrocarbons following laser volumertric heating by: doping the feed stock with an absorbing gas such as ethylene to absorb laser radiation in a controlled manner: applying laser radiation in the form of a sheet with a thickness from about 5 to about 20 mm perpendicular to the flow direction of the feed stock; maintaining a reaction temperature around 1800° to 200° K by adjusting the energy output of the laser; and maintaining the temperature of the reaction chamber walls below 1000° K.

7 Claims, 3 Drawing Figures

METHOD FOR PRODUCTION OF ACETYLENE BY LASER IRRADIATION

BACKGROUND OF THE INVENTION

This invention is directed to the production of acetylene and more particularly to the production of acetylene by the use of a laser beam for volumetric heating of the hydrocarbon feed stock.

It is well known that acetylene has widespread use in welding and in the manufacture of an increasing number of industrial chemicals such as plastics and acetic acid. Acetylene has been produced by the use of calcium carbide and through the pyrolysis of natural gas. An efficient method using natural gas relies on electric arc heating in combination with a magnetic field to rotate and control the arc. Such a system has been set forth in U.S. Pat. No. 3,073,769. In the electric arc method, the electric arc heats the walls where it strikes the wall surface, and the core of the rotating arc is much hotter than the desired reaction temperature. The arc method thus produces hot spots which have deleterious effects on the acetylene production.

SUMMARY OF THE INVENTION

This invention makes use of a laser beam, narrow in the flow direction, but broad in the direction transverse to the flow, for rapid pyrolytic cracking of hydrocarbons to produce acetylene. The use of a laser beam eliminates the requirements for a magnetic field, an arc, and carbon electrodes as used in the prior art. Thus, the present method avoids the carbon buildup problem, provides more rapid heating, eliminates occasional catastrophic failure due to arc instability, and provides a much simpler device and a more efficient method which produces fewer by-products. The present system does not produce hot spots; therefore, it reduces side and heterogeneous reactions.

DETAILED DESCRIPTION

In carrying out the method of this invention, a gaseous hydrocarbon input is fed into a preheater section where the gaseous input is heated to a point at which a slow rate of reaction occurs. The preheated gases pass to a quick-heat section where the preheated gaseous input is heated volumetrically by a laser beam perpendicular to the gas stream to produce the conditions necessary for a gaseous reaction. From the quick-heat section, the gases pass quickly through a reaction zone where the desired reactions occur and then to a quench section where the quick-heated gas is rapidly quenched by a liquid, such as water or heavy hydrocarbon spray. The mixture of the quench material and reaction gases is passed to an entrainment tank where the gaseous and liquid phases are separated.

Figure 1:
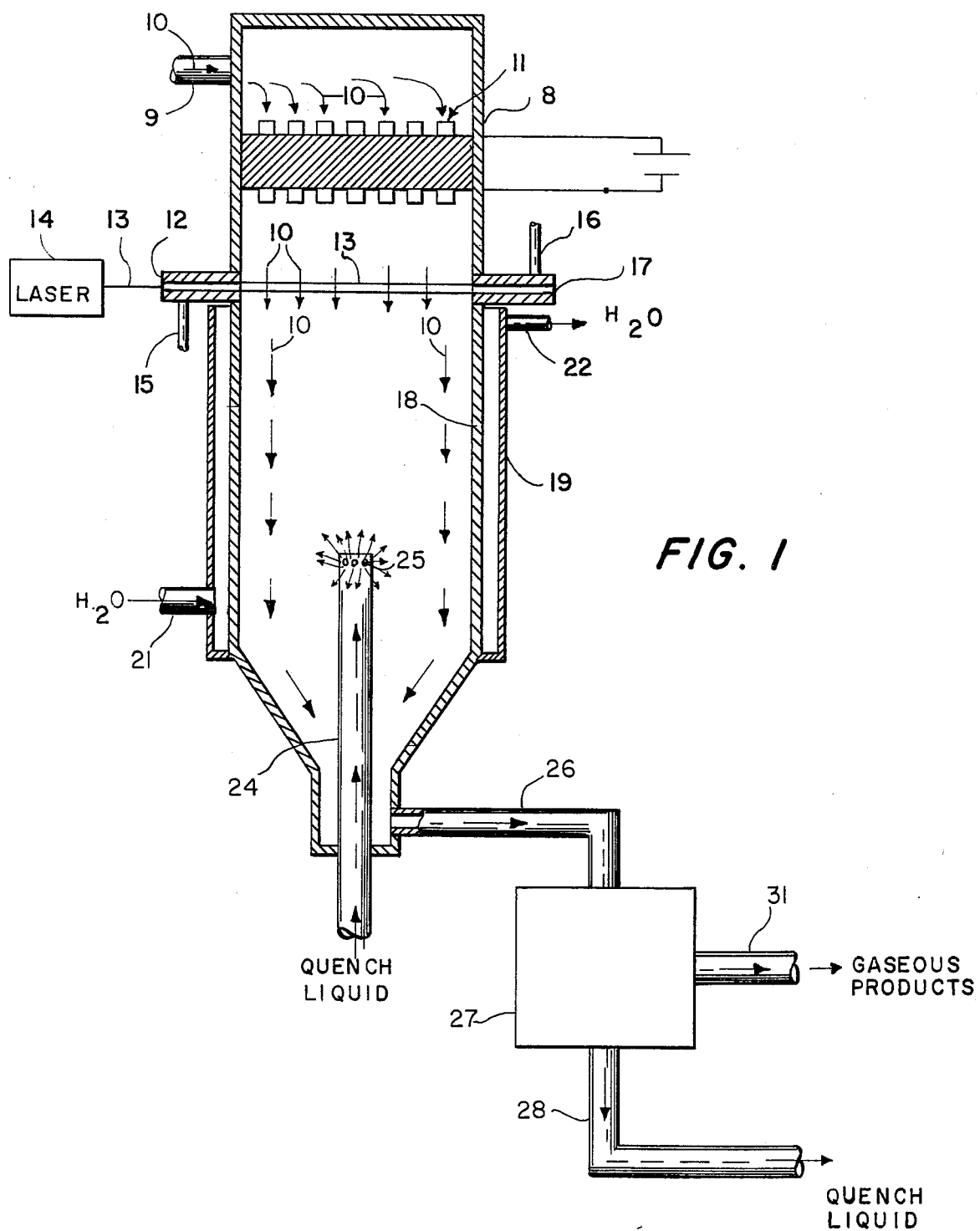
FIG. 1 illustrates a suitable system for carrying out the method of this invention.
Figure 2:
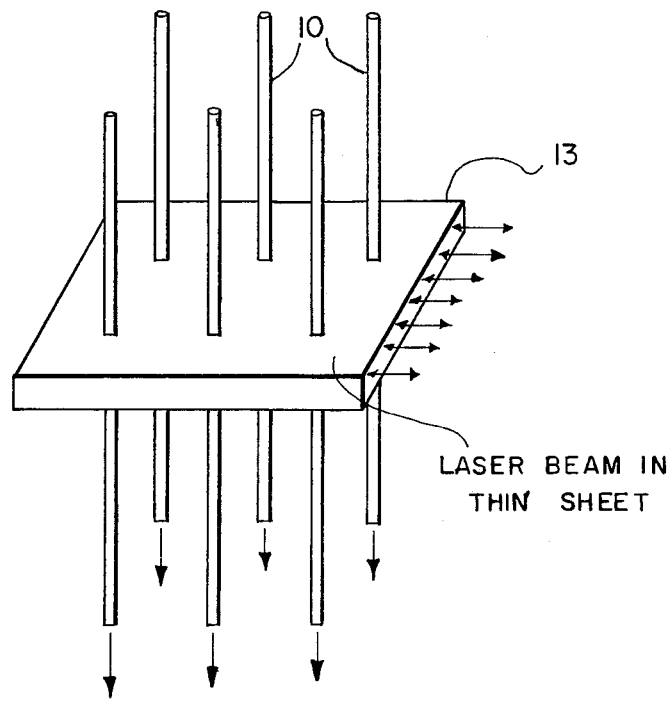
FIG. 2 broadly illustrates gas flow with a laser beam directed across the flow path.

Now, referring to the drawing, FIG. 1 shows a system suitable for carrying out the method of this invention. The system includes a gas inlet 9 for introducing gas 10 into a preheater 11 in housing 8 where the gas is preheated to a desired temperature by any suitable means. An electrical heater means has been shown, which may be of any suitable type. Below the heater, the device includes an optical window 12 through which laser radiation 13 produced by laser 14 passes. Window purge gas enters through inlets 15 and 16 as shown. The laser radiation is reflected by a mirror 17 for uniform deposition and is shaped to be in the form of a wide beam having a thickness of from about 5 mm to about 20 mm such as shown in FIG. 2.

As shown in FIG. 1, the laser beam is directed horizontally, across the housing and the direction of the gas is vertically downward, parallel with the surface of the paper. As such, the laser beam is perpendicular to the gas flow.

The beam is made wide in the direction across the housing to permit large total flow rates. The portion of the device below the optical window 12 is the reaction zone and is comprised of an inner wall 18 and an outer wall 19 which forms a jacket through which a heat exchange medium such as steam is fed through an inlet 21 and outlet 22 to keep the temperature of the inner wall below 1000° K. The bottom of the housing is funnel-shaped and has a pipe 24 inserted into the housing from the bottom and coaxial therewith. The pipe 24 is provided with spray apertures 25 on the upper end thereof through which water or other liquid is sprayed to rapidly quench the gaseous reaction. The bottom of the housing is closed off and is provided with an outlet 26 that connects with an entrainment tank 27 in which the gases are separated from the quenching liquid. The liquid passes from the tank 27 through outlet 28 while the gases pass from the tank through outlet 31.

In operation to carry out the method, the hydrocarbon feed gas is fed through inlet 9 into the preheater 11 at a pressure of several atmospheres. The feed gas is doped with gas such as an olefin, which absorbs the laser radiation in a controlled manner. The gases are preheated to a temperature of about 1300° K by the preheater. The preheated gases flow from the preheater area in an axial direction and pass the optical window area, through the laser beam, which is directed across the chamber perpendicular to the gas flow path. As the gas passes through the laser beam, the gas is immediately volumetrically heated to the desired temperature of about 1800° K during the short time the gas is in the beam.

Figure 3:
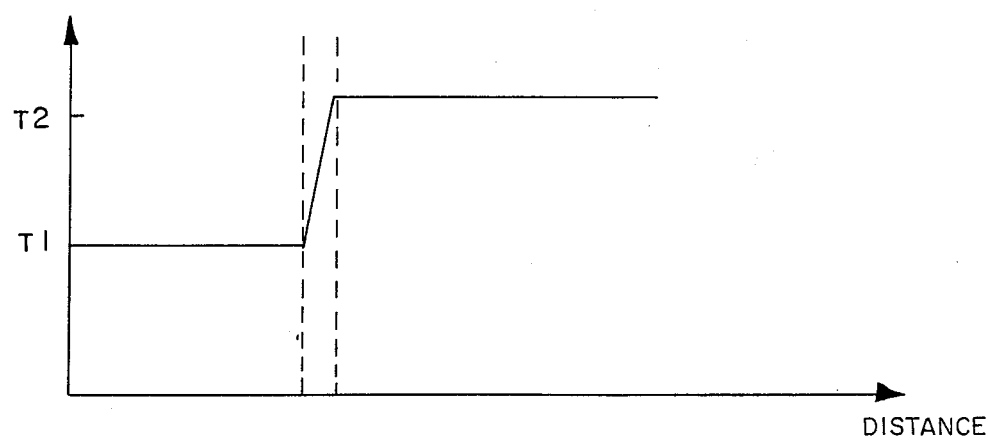
FIG. 3 illustrates the temperature curve of the gas flow before and after excitation by the laser beam.

FIG. 3 illustrates the temperature curve before, during, and after passing through the laser beam. The hydrocarbon gas is pyrolyzed to acetylene, hydrogen, and other by-products. After a short time (0.01 sec) when sufficient reaction has occurred, the gaseous reaction mixture is quenched by a liquid spray admitted through pipe 24 and nozzle 25. The gaseous reaction-quench liquid mixture flows from the bottom of the chamber out through outlet pipe 26 to the entrainment tank 27 in which the quench liquid and gases are separated. The gases flow through outlet pipe 31 to a storage tank or to a system for separating gases which forms no part of this invention. The quench liquid is discharged through outlet pipe 28 to a holding tank for further use or to waste disposal means. During operation, the reaction area walls should be maintained at about 1000° K by the steam which flows through the jacket formed by walls 18 and 19. The heat added to this steam can be recycled to the preheat section or used elsewhere.

The device has been described using a hydrocarbon gas for forming acetylene. It is obvious that the device may be used to form acetylene from other gases or feed stock. The device is not limited for forming acetylene but may be used for rapid heating and cooling of any desired reaction products.

Obviously many modifications and variations of the present invention are possible in light of the above teachings. It is therefore to be understood that within the scope of the appended claims the invention may be practiced otherwise than as specifically described.

What is claimed and desired to be secured by letters patent of the United States is:

1. A method for pyrolytic production of acetylene which comprises:
   doping a hydrocarbon gas with an olefin to absorb laser radiation in a controlled manner; and
   irradiating said doped hydrocarbon gas with laser radiation to quickly raise said gas to a reaction temperature at which acetylene is produced.

2. A method as claimed in claim 1 in which:
   said doped hydrocarbon gas is preheated prior to being irradiated by said laser radiation.

3. A method as claimed in claim 2 wherein:
   subsequent to quickly heating said hydrocarbon gas, said gas is rapidly quenched by a quenching liquid directed into the gas flow.

4. A method as claimed in claim 3 wherein:
   said quenching fluid is separated from said produced gases.

5. A method as claimed in claim 1 wherein:
   said gas is raised to a temperature of about $1800°-2000°$ K by said laser radiation during its reaction period.

6. A method as claimed in claim 5 which includes:
   maintaining the walls of the reaction area at a temperature of not more than $1000°$ K.

7. A method as claimed in claim 1 wherein said olefin is ethylene.

* * * * *